US011229730B2

(12) United States Patent
Teo et al.

(10) Patent No.: US 11,229,730 B2
(45) Date of Patent: Jan. 25, 2022

(54) DIALYSIS ACCESS

(71) Applicant: Kaxon Care, Inc., Kearns, UT (US)

(72) Inventors: Carlie Teo, Kearns, UT (US); Whitney Heinzig, American Fork, UT (US)

(73) Assignee: KAXON CARE, INC., Kearns, UT (US)

( * ) Notice: Subject to any disclaimer, the term of this patent is extended or adjusted under 35 U.S.C. 154(b) by 114 days.

(21) Appl. No.: 16/591,592

(22) Filed: Oct. 2, 2019

(65) Prior Publication Data

US 2020/0101216 A1    Apr. 2, 2020

Related U.S. Application Data

(60) Provisional application No. 62/740,228, filed on Oct. 2, 2018.

(51) Int. Cl.
*A61M 25/06* (2006.01)
*A61M 25/02* (2006.01)
*A61M 1/36* (2006.01)

(52) U.S. Cl.
CPC .......... *A61M 1/3661* (2014.02); *A61M 25/02* (2013.01); *A61M 25/0606* (2013.01); *A61M 25/0618* (2013.01); *A61M 25/0637* (2013.01); *A61M 2025/0266* (2013.01)

(58) Field of Classification Search
CPC .. A61M 25/06; A61M 25/01; A61M 25/0606; A61M 1/3661; A61M 25/0637; A61M 25/0618; A61M 25/02; A61M 2025/0266; A61M 25/007
See application file for complete search history.

(56) References Cited

U.S. PATENT DOCUMENTS

| | | | |
|---|---|---|---|
| 4,333,455 A | 6/1982 | Bodicky | |
| 5,607,407 A | 3/1997 | Tolkoff et al. | |
| 5,743,891 A * | 4/1998 | Tolkoff | A61M 5/3273 604/164.01 |
| 6,506,182 B2 | 1/2003 | Estabrook et al. | |
| 9,233,230 B2 * | 1/2016 | Puhasm | A61M 1/3661 |
| 2003/0149395 A1 * | 8/2003 | Zawacki | A61M 1/3653 604/40 |
| 2005/0273076 A1 | 12/2005 | Beasely | |
| 2012/0323181 A1 * | 12/2012 | Shaw | A61B 17/3415 604/164.12 |

FOREIGN PATENT DOCUMENTS

DE    102007028367 A1 *  12/2008  ........ A61M 25/0606

* cited by examiner

*Primary Examiner* — Phillip A Gray
(74) *Attorney, Agent, or Firm* — Miller IP Law

(57) ABSTRACT

A dialysis access is disclosed. The dialysis access includes a tubular base, an initial access structure, a persistent access structure, and a seal. The initial access structure is retractably disposed within an interior of the tubular base and includes a piercing tip. The initial access structure is retractable from an extended position to a withdrawn position. The persistent access structure is coupled to the tubular base and surrounds and extends along a length of the initial access structure with the piercing tip exposed while in the extended position. The persistent access structure remains stationary relative to the base with the initial access structure in the withdrawn position. The seal is disposed within the tubular base to surround the initial access structure while in the extended position and to isolate the initial access structure from a fluid flow path within the tubular base while in the withdrawn position.

20 Claims, 8 Drawing Sheets

DIALYSIS ACCESS

CROSS-REFERENCE TO RELATED APPLICATION

This application claims the benefit of U.S. Provisional Patent Application No. 62/740,228, entitled "DIALYSIS ACCESS" and filed on 2 Oct. 2018, for Carlie Teo and Whitney Heinzig, which is incorporated herein by reference.

FIELD

This invention relates to access to the body for medical treatments or procedures and more particularly relates to access to the body for dialysis treatment.

BACKGROUND

For dialysis and other medical treatments or procedures, access to the circulatory system, or other component of the body, is necessary or improves the effectiveness of the treatments or procedures. However, establishing and maintaining access to the circulatory system can be painful or present risk of injury or other complications. In some cases, establishing and maintaining the access can require surgery and providing repeated or routine access can damage the access location, which can cause harm or discomfort to the caregiver or the patient.

SUMMARY

A dialysis access apparatus (i.e., dialysis access) is disclosed. The dialysis access includes a tubular base, and initial access structure, a persistent access structure, and a seal. The initial access structure is retractably disposed within an interior of the tubular base. The initial access structure includes a piercing tip at a distal end of the initial access structure. The initial access structure is retractable from an extended position to a withdrawn position relative to the tubular base. The persistent access structure is coupled to the tubular base. The persistent access structure surrounds and extends along a length of the initial access structure with the piercing tip exposed while the initial access structure is in the extended position. The persistent access structure remains stationary relative to the base with the initial access structure in the withdrawn position. The seal is disposed within the tubular base. The seal is configured to surround the initial access structure while the initial access structure is in the extended position and to isolate the initial access structure from a fluid flow path within the tubular base while the initial access structure is in the withdrawn position.

A method is also disclosed. The method includes inserting a dialysis access at a treatment location with an initial access structure in an extended position. The method also includes withdrawing the initial access structure to a withdrawn position leaving a persistent access structure in place at the treatment location. The method also includes performing a treatment. The method also includes removing the dialysis access from the treatment location.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Figure 1:
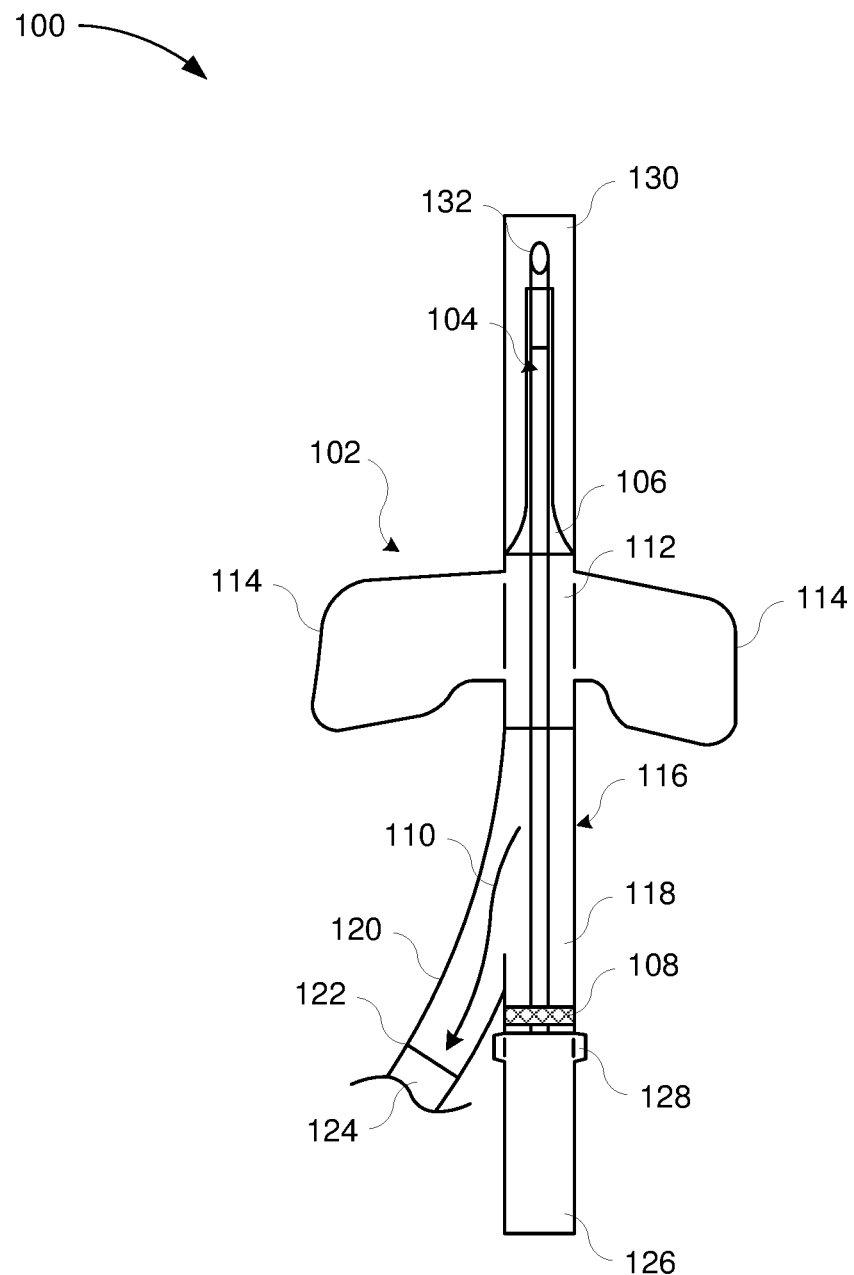
FIG. 1 is a schematic view illustrating one embodiment of a dialysis access.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Embodiments described herein relate to an improved dialysis access. Embodiments of the improved dialysis access provide a device, system, and method for establishing dialysis access with the advantage of an initial access structure that can be withdrawn to leave a persistent access structure for a patient treatment duration that is more comfortable and safer than the initial access structure and provides guards and safeties to reduce patient and caregiver risk of harm.

FIG. 1 illustrates an elevation view of one embodiment of a dialysis access 100. The illustrated embodiment includes a tubular base 102. An initial access structure 104 is retractably disposed within the tubular base 102. The initial access structure 104 is retractable from an extended position to a withdrawn position relative to the tubular base 102. In the illustrated embodiment, the initial access structure 104 is in the extended position relative to the tubular base 102.

A persistent access structure 106 is coupled to the tubular base 102. The persistent access structure 106 surrounds at least a portion of the initial access structure 104 and extends along a length of the initial access structure 104. A seal 108 is disposed within the tubular base 102. The seal 108 surrounds the initial access structure 104 while the initial access structure 104 is in the extended position and isolates the initial access structure 104 from a fluid flow path 110 within the tubular base 102 while the initial access structure 104 is in the withdrawn position.

In some embodiments, the tubular base 102 includes a wing portion 112. The wing portion 112 includes wings 114. The wings 114 may be coupled to the wing portion 112, form a unified part of the wing portion 112, or form a part of a collar or other structure which may be coupled to the wing portion 112. The wings 114 may take any form including the one shown in FIG. 1. The wings 114 may provide a location to grip the dialysis access 100 when applying the dialysis access 100 to a user. Additionally, the wings 114 may provide a location to adhere a tape or wrap to secure the dialysis access 100 on the user. In some embodiments, the wings 114 may be textured, have surface features, or the like to provide grip for fingers, gloves, tapes, wraps, or the like.

The illustrated embodiment of the tubular base 102 includes a junction portion 116. The junction portion 116 is a portion of the tubular base 102 next to the wing portion 112. The junction portion 116 may be bonded to the wing portion 112 or form a portion of a single-piece tubular base 102. In the illustrated embodiment, the junction portion 116 includes a withdrawal leg 118 and a fluid flow leg 120. The withdrawal leg 118 is aligned with the initial access structure 104 and forms a continuous extension of the tubular base 102 to allow for withdrawal of the initial access structure 104. The fluid flow leg 120 branches off from the tubular base 102 and forms a portion of the fluid flow path 110 that is apart from the initial access structure 104.

In some embodiments, the fluid flow leg 120 includes an attachment point 122 for attaching a line 124 to the dialysis access 100. The attachment point 122 may be a luer lock, a threaded connection, a click lock, or the like. The line 124 may be a rigid or flexible hollow member for carrying fluid to, and/or away from, the dialysis access 100.

In the illustrated embodiment, the withdrawal leg 118 includes the seal 108. The seal 108 forms a closure against the initial access structure 104 in the extended position and closes off the end of the withdrawal leg 118 of the junction portion 116 of the tubular base 102 when the initial access structure is withdrawn from the tubular base 102. In both instances, the seal 108 prevents fluid from exiting the dialysis access 100 via the withdrawal leg 118. Embodiments of the seal 108 are described in more detail below in relation to FIGS. 5 and 6.

In the illustrated embodiment of FIG. 1, the dialysis access 100 also includes a base cap 126. The base cap 126 is coupled to the initial access structure 104. The base cap 126 is uncoupleable from the tubular base 102 to withdraw the initial access structure 104 and leave the persistent access structure 106 in place. The base cap 126 may include a locking mechanism 128 to secure the end cap 126 and, by extension, the initial access structure 104, relative to the tubular base 102. The locking mechanism 128 may be a clip, threads, latch, catch, ridge, or the like.

The illustrated embodiment of the dialysis access 100 also includes a safety cap 130. The safety cap 130 couples to the tubular base 102 and covers the initial access structure 104 and the persistent access structure 106. This both protects from an accidental stick and maintains the initial access structure 104 and the persistent access structure 106 clean. In some embodiments, the safety cap 130 includes a locking mechanism (not shown) similar to those described above with reference to the locking mechanism 128 of the end cap 126. The safety cap 130 is configured to extend past a piercing tip 132 of the initial access structure 104. Because the piercing tip 132 is sharp and should remain sharp, the safety cap 130 provides clearance for the piercing tip 132 to reduce the likelihood of accidental blunting of the piercing tip 132 and/or potential injury to a user.

Figure 2:
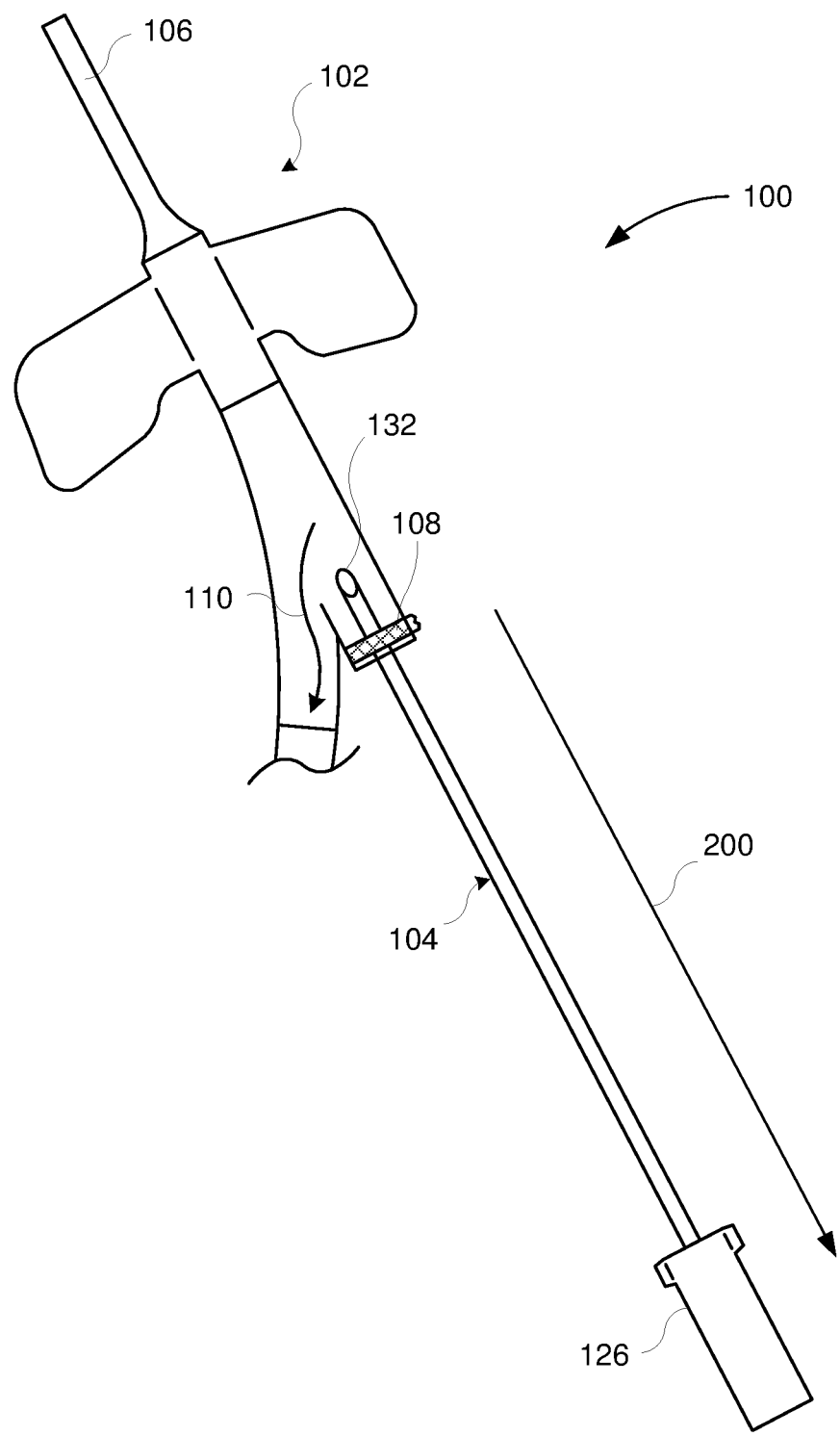
FIG. 2 is a schematic view illustrating one embodiment of the dialysis access of FIG. 1 with the initial access structure in a partially withdrawn position.

FIG. 2 illustrates an elevation view of one embodiment of the dialysis access 100 of FIG. 1 with the initial access structure 104 in the withdrawn position 200. In the illustrated embodiment, the safety cap 130 is removed and the withdrawn position 200 is reached with the initial access structure 104 withdrawn from the tubular base 102 sufficient to remove the piercing tip 132 from the fluid flow path 110.

In the illustrated embodiment, the persistent access structure 106 remains in place with the initial access structure 104 drawn back to the withdrawn position 200. In some embodiments, the persistent access structure 106 is left in place for the duration of a treatment or procedure while the initial access structure 104 is withdrawn to the illustrated withdrawn position 200. The persistent access structure 106 may provide a more flexible access for a patient to reduce damage, wear, or discomfort for a user.

In the illustrated embodiment, the seal 108 prevents fluid from exiting the dialysis access 100 around the initial access structure 104. In some embodiments, the seal 108 further includes a retaining feature which interfaces with the initial access structure 104 to retain or resist complete withdrawal of the initial access structure 104. In other embodiments, the seal 108 allows the initial access structure 104 to be completely withdrawn and resists fluid penetration after the initial access structure 104 is removed.

Figure 3:
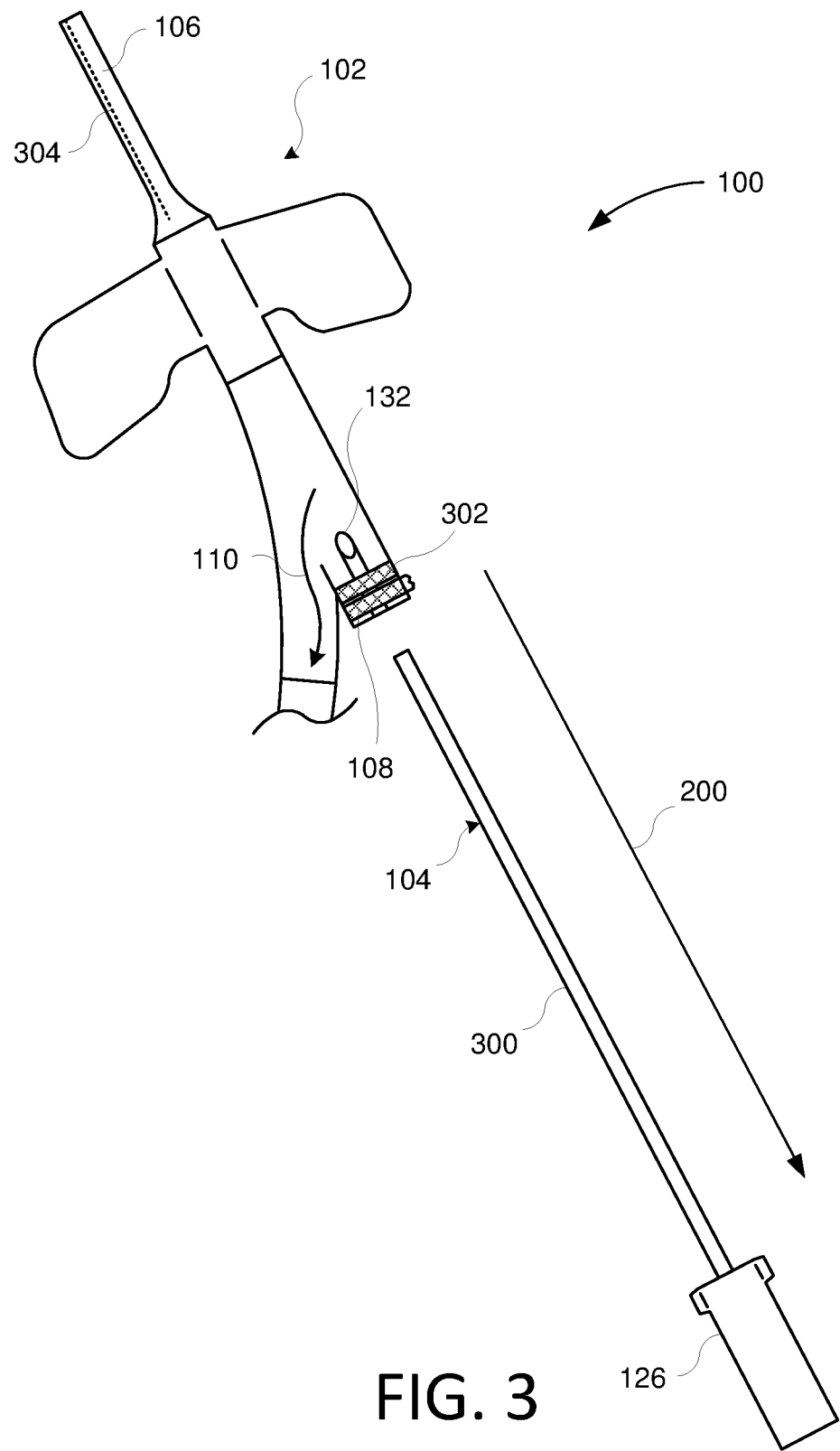
FIG. 3 is a schematic view illustrating one embodiment of the dialysis access of FIG. 1 with the initial access structure in a withdrawn position and a piercing tip captured.

FIG. 3 illustrates an elevation view of one embodiment of the dialysis access 100 of FIG. 1 with the initial access structure 104 in the withdrawn position 200. In the illustrated embodiment, the piercing tip 132 is separable from a stem 300 of the initial access structure 104. In some embodiments, the piercing tip 132 is engaged and held by a retaining feature 302. In some embodiments, the retaining feature 302 is proximate the seal 108. In other embodiments, the retaining feature 302 is integrated with the seal 108. For example, the retaining feature 302 may be integrated or coupled to one side of the seal 108 or another or the retaining feature 302 may be integrated internal to the seal 108.

The stem 300 may be separable from the piercing tip 132. In some embodiments, the piercing tip 132 is sufficiently long to provide a working surface for the initial access structure 104. In other words, in some embodiments, the stem 300 does not contact the tissue of a patient or user. In some embodiments, the piercing tip 132 is a rigid material capable of maintaining a point. For example, the piercing tip may include metal, ceramic, glass, or the like. In some embodiments, the stem 300 includes one or more materials that are different from that of the piercing tip 132. For example, the stem 300 may include a plastic, composite, or the like.

In some embodiments, at least one of the piercing tip 132 and the stem 302 are solid. In other words, some embodiments of the initial access structure 104 include a piercing tip 132 and/or a stem 302 that is not hollow. In some embodiments, in may be useful to allow fluid flow into the tubular base 102 once the dialysis access 100 is positioned properly in a fistula, graft, vein, or the like, to indicate an access or placement state. In the illustrated embodiment, the persistent access structure 106 includes a channel 304 to facilitate fluid flow past the initial access structure 104 while the initial access structure 104 is in the extended position (as shown in FIG. 1). In other embodiments, at least one of the piercing tip 132 and the stem 300 include a channel (not shown) which runs at least a partial length of the at least one of the piercing tip 132 and the stem 300.

Figure 4:
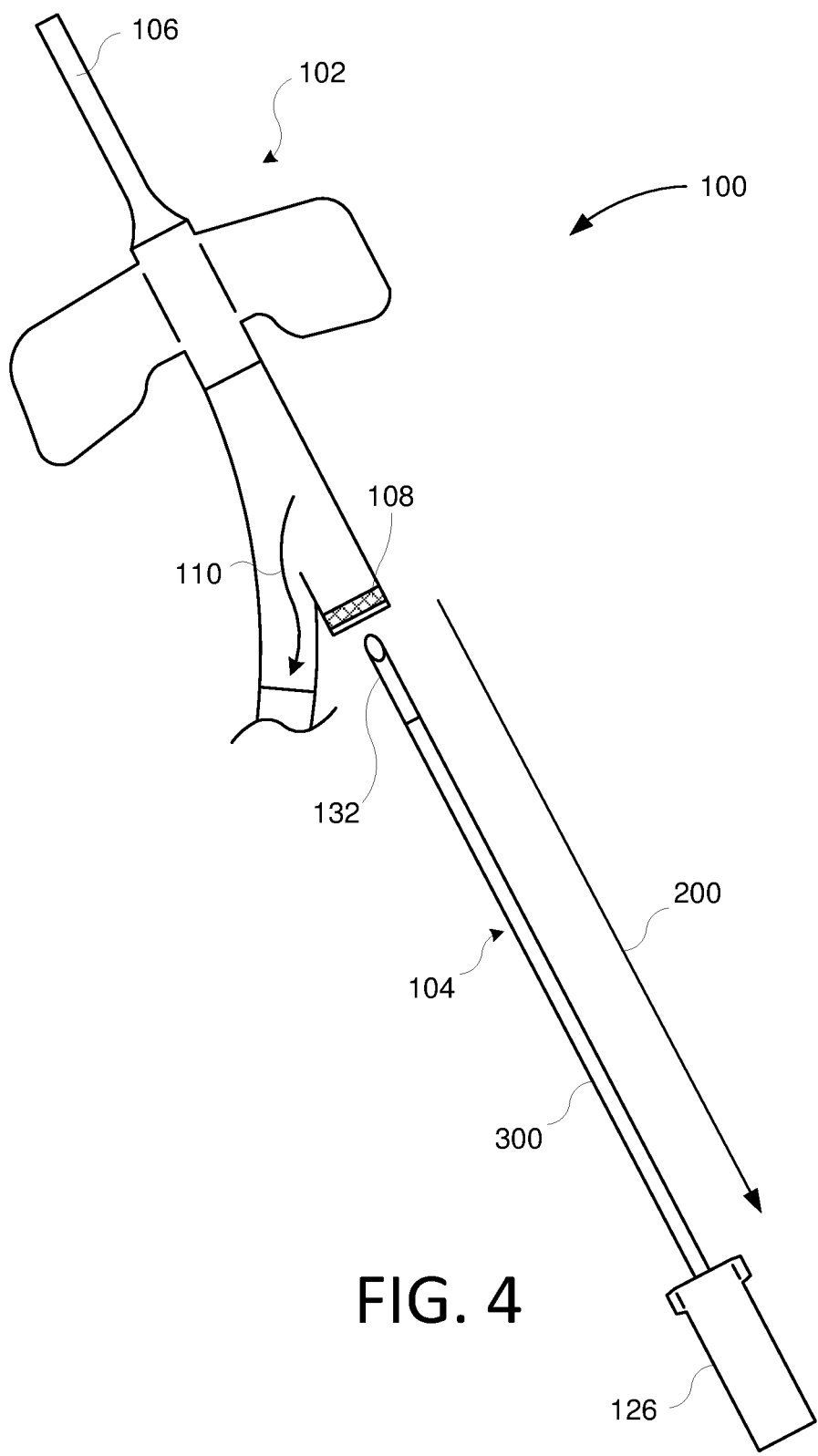
FIG. 4 is a schematic view illustrating one embodiment of the dialysis access of FIG. 1 with the initial access structure in a withdrawn position without capture.

FIG. 4 illustrates an elevation view of one embodiment of the dialysis access 100 of FIG. 1 with the initial access structure 104 in the withdrawn position 200. In the illustrated embodiment, the initial access structure 104 is completely withdrawn from the tubular base 102. In the illustrated embodiment, the initial access structure 104 remains intact with the piercing tip 132 coupled to the stem 300. The stem 300 remains coupled to the end cap 126.

Figure 5:
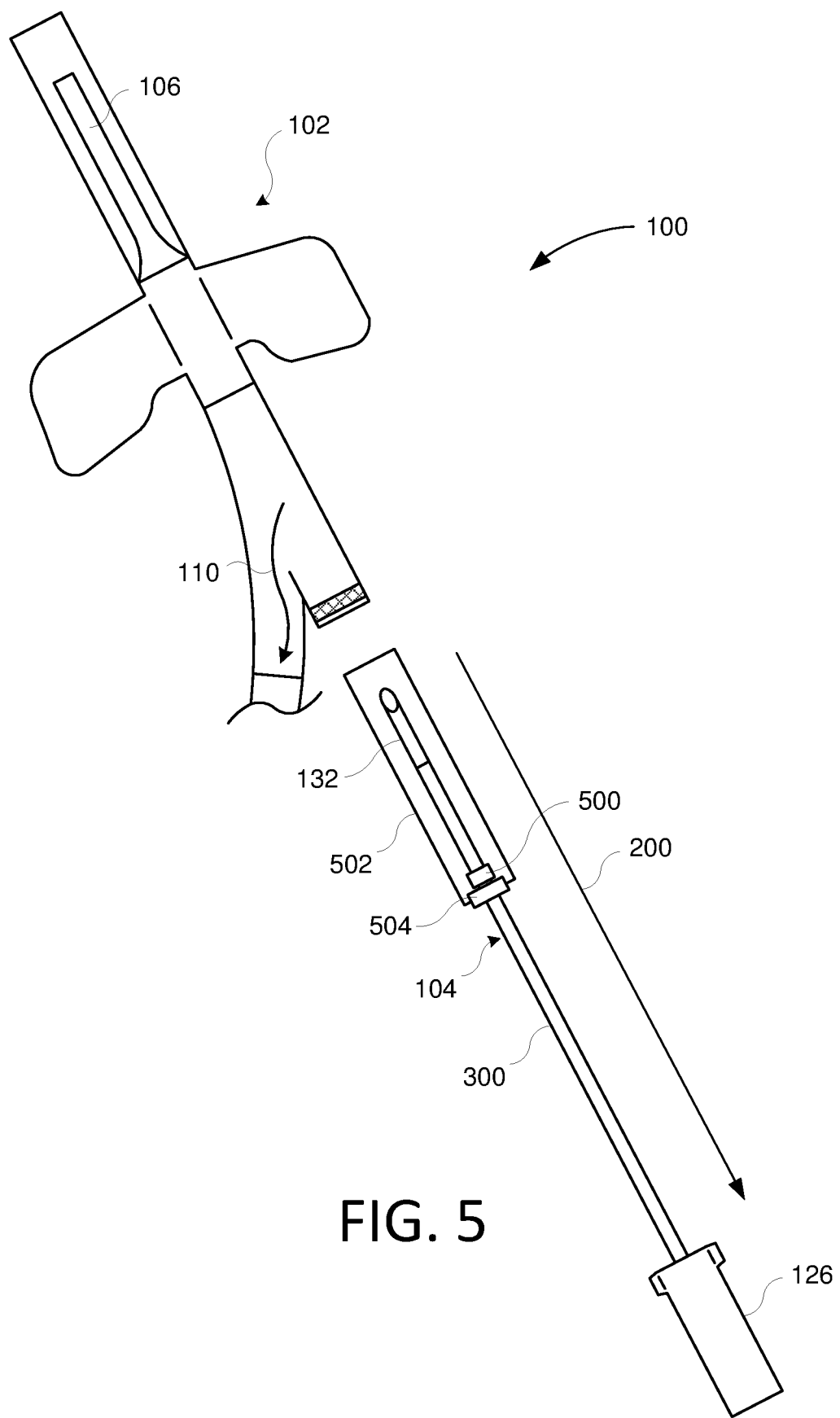
FIG. 5 is a schematic view illustration one embodiment of the dialysis access of FIG. 1 with the initial access structure in a withdrawn position with a safety sleeve.

FIG. 5 illustrates an elevation view of one embodiment of the dialysis access 100 of FIG. 1 with the initial access structure 104 in the withdrawn position 200. In the illustrated embodiment, the initial access structure 104 includes a catch 500. In the illustrated embodiment, the catch 500 is positioned on the stem 300. In other embodiments, the catch 500 is positioned on the piercing tip 132. The catch 500 may be positioned and sized to interface with a safety sleeve 502. In some embodiments, the safety sleeve 502 is integrated with the tubular base 102 until the initial access structure 104 is withdrawn. In other embodiments, the safety sleeve 502 may be all or part of the safety cap 130, as shown in FIG. 1. In some embodiments, the safety sleeve 502 may be a separate component from the safety cap 130 and separate from the tubular base 102.

In the illustrated embodiment, the safety sleeve 502 includes a catch receiver 504. The catch receiver 504 may interface with the catch 500 or with another portion of the stem 300 or the piercing tip 132. In some embodiments, the catch receiver 504 releasably holds the initial access structure 104 to prevent the piercing tip 132 from being exposed outside of the safety sleeve 502. In some embodiments, the catch receiver 504 is unreleasable.

Figure 6:
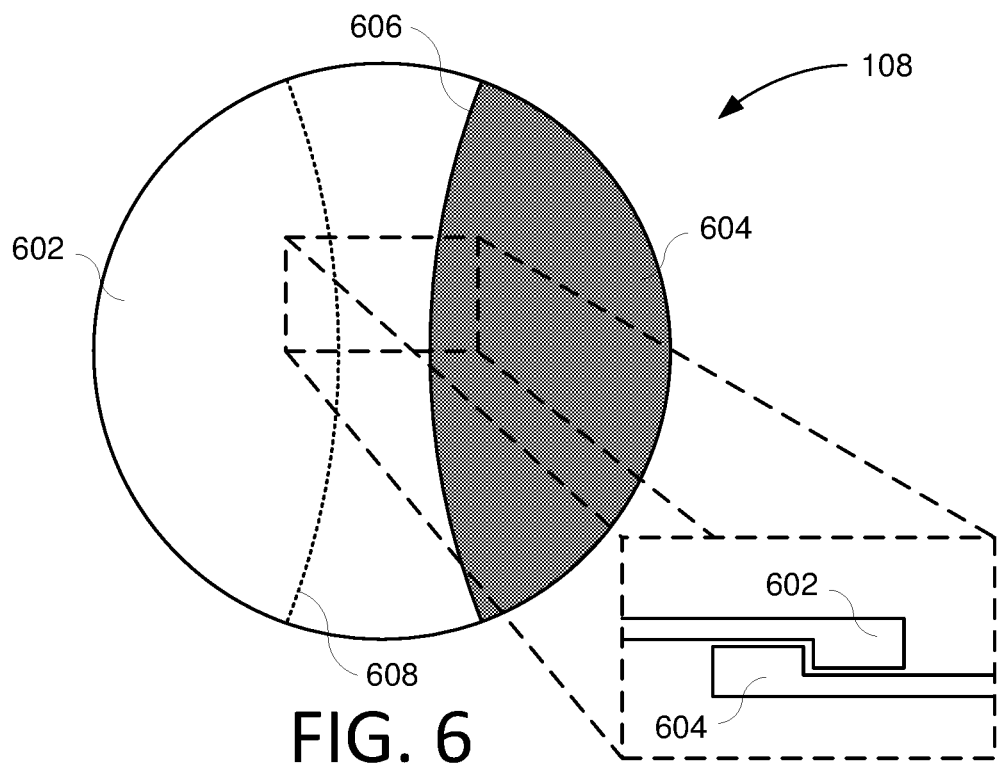
FIG. 6 illustrates a front view of one embodiment of a seal of FIG. 1 with the initial access structure in a withdrawn position.

FIG. 6 illustrates a front view of one embodiment of the seal 108 of FIG. 1 with the initial access structure 104 withdrawn. The illustrated embodiment includes a first membrane 602 and a second membrane 604. The first membrane 602 is sized and positioned such that an outer edge 606 of the first membrane 602 overlaps the second membrane 604. Similarly, the second membrane 604 is sized and positioned such that an outer edge 608 of the second membrane 608 overlaps the first membrane 602.

The seal 108 forms a closure around the initial access structure 104 in the extended position and closes off the tubular base 102 when the initial access structure 104 is completely withdrawn. At least a portion of the seal 108 includes a flexible material. The material may be a synthetic material, a natural material, or a combination thereof. While the first membrane 602 and the second membrane 604 are shown with curved edges 606 and 604, other shapes and geometries may be used to form a seal with the initial access structure 104 and after the initial access structure 104 is withdrawn. For example, the membranes 602 and 604 may include a notched feature or a straight edge. As shown, the first membrane 602 and the second membrane 604 may interlock with one another to provide improved sealing characteristics or tolerate pressure in the fluid flow. In some embodiments, a rigid material may be incorporated into one or more of the membranes 602 and 604. While the membranes 602 and 604 are shown as having a similar geometry, in some embodiments, the membranes 602 and 604 may be dissimilar from one another.

Figure 7:
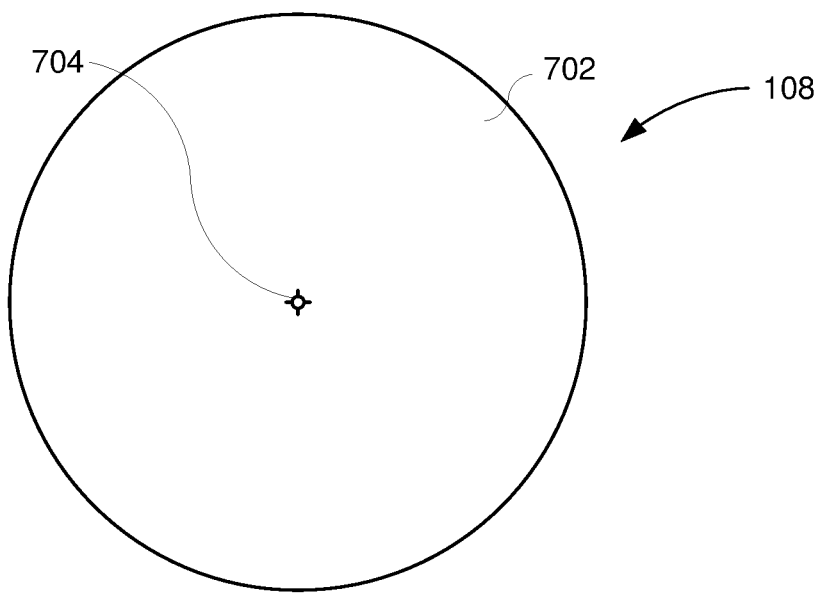
FIG. 7 illustrates a front view of another embodiment of the seal of FIG. 1 with the initial access structure in a withdrawn position.

FIG. 7 illustrates a front view of another embodiment of the seal 108 of FIG. 1 with the initial access structure 104 withdrawn. In the illustrated embodiment a single membrane 702 is shown. The illustrated single membrane 702 spans the entirety seal 108. The illustrated embodiment of the seal 108 also includes a flexible aperture 704. The flexible aperture 704 facilitates passage of the initial access structure 104 while maintaining a barrier to fluid flow past the seal 108. The flexible aperture 704 contracts in response to withdrawal of the initial access structure 104 to close the seal 108 and form a complete barrier that is resistant to fluid flow past the seal 108. In some embodiments, the contraction of the aperture 704 is achieved by an elastic characteristic of the single membrane 702. In other embodiments, other characteristics of the membrane 702, for example, chemical, mechanical, and the like, facilitate operation of the aperture 704.

Figure 8:
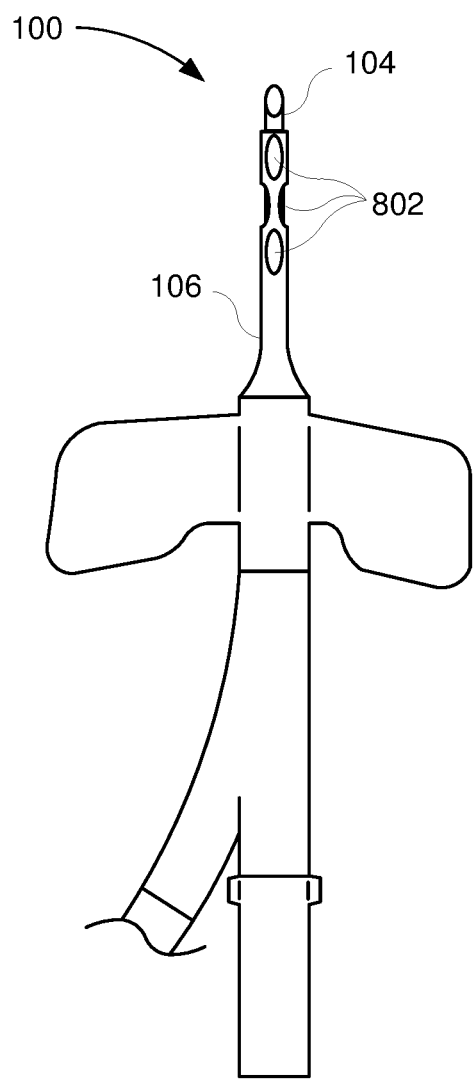
FIG. 8 illustrates a schematic view of one embodiment of the dialysis access of FIG. 1 with one embodiment of a persistent access structure.

FIG. 8 illustrates an elevation view of one embodiment of the dialysis access 100 of FIG. 1. The illustrated embodiment includes a persistent access structure 106 with one or more backeyes 802 formed in the persistent access structure 106. The backeyes 802 facilitate greater flow into and out of the dialysis access 100 by reducing the chance of tissue blocking, back-walling, plugging, and the like. In the illustrated embodiment, the backeyes 802 are staggered along the length of the persistent access structure 106. In other embodiments, the backeyes 802 may be larger or smaller and may be organized in another pattern or arrangement in the persistent access structure 106. The backeyes 802 may be positioned strategically to at least one of facilitate fluid flow, to add flexibility and/or rigidity, to reduce drag during insertion and/or removal, improve user comfort during treatment, and facilitate withdrawal of the initial access structure 104.

Figure 9:
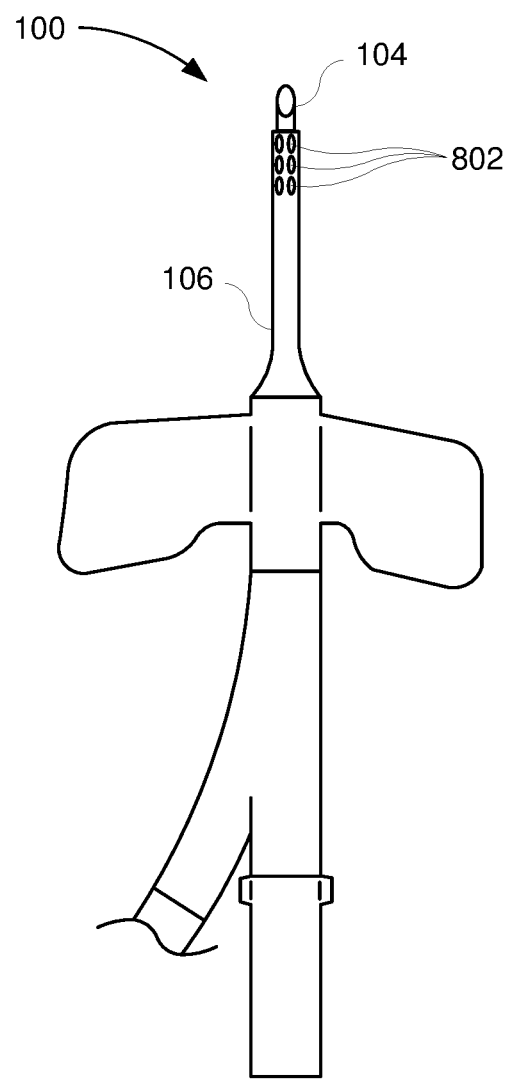
FIG. 9 illustrates a schematic view of one embodiment of the dialysis access of FIG. 1 with another embodiment of the persistent access structure.

FIG. 9 illustrates an elevation view of another embodiment of the dialysis access 100 of FIG. 1. The illustrated embodiment includes the persistent access structure 106 with one or more backeyes 802 arranged around the persistent access structure 106 to be near the initial access structure 104. In some embodiments, the backeyes 802 have a chamfered or rounded edge to prevent tissue drag, irritation, and damage during insertion, treatment, and removal. In some embodiments, the backeyes 802 include fluid soluble plugs which fill the backeyes 802 and dissolve in response to exposure to fluid flow, body heat, or other environmental conditions or stimulus associated with dialysis treatment. Other features and characteristics of the backeyes 802 are contemplated.

Figure 10:
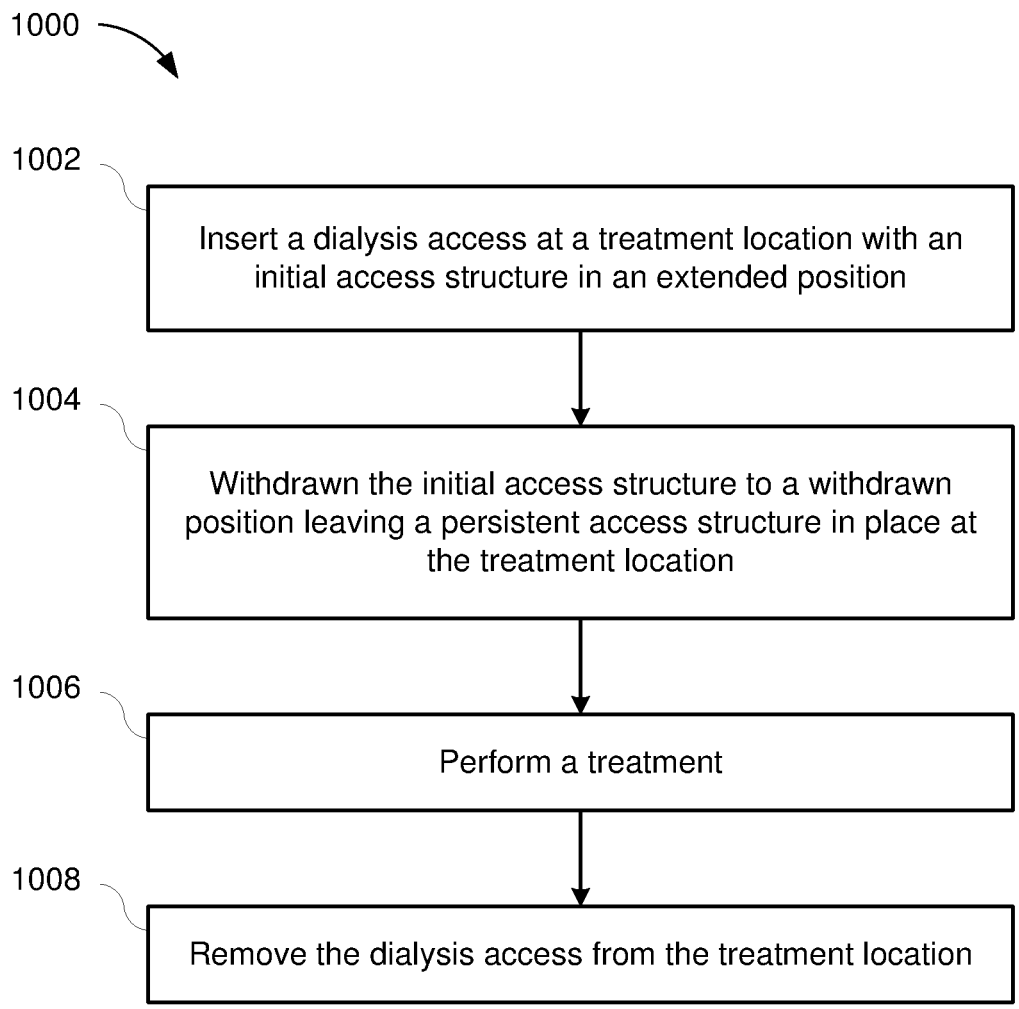
FIG. 10 is a schematic block diagram illustrating one embodiment of a method of using a dialysis access.

FIG. 10 includes a method 1000. The method 1000 includes inserting 1002 a dialysis access at a treatment location with an initial access structure in an extended position. The method 1000 also includes withdrawing 1004 the initial access structure to a withdrawn position leaving a persistent access structure in place at the treatment location. The method 1000 also includes performing 1006 a treatment. The method 1000 also includes removing 1008 the dialysis access from the treatment location.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dialysis access comprising:
    a tubular base;
    an initial access structure retractably disposed within an interior of the tubular base, the initial access structure comprising a piercing tip at a distal end of the initial access structure, the initial access structure retractable from an extended position to a withdrawn position relative to the tubular base;
    a persistent access structure coupled to the tubular base, the persistent access structure surrounding and extending along a length of the initial access structure with the piercing tip exposed while the initial access structure is in the extended position, wherein the persistent access structure remains stationary relative to the tubular base with the initial access structure in the withdrawn position;
    a seal disposed within the tubular base, the seal being configured to surround the initial access structure while the initial access structure is in the extended position and to isolate the initial access structure from a fluid flow path within the tubular base while the initial access structure is in the withdrawn position; and
    a retaining feature disposed proximate the seal to capture the piercing tip of the initial access structure at the seal and on a same side of the seal as the persistent access structure.

2. The dialysis access of claim 1, wherein the initial access structure is uncoupleable from the tubular base in the withdrawn position.

3. The dialysis access of claim 1, further comprising a removeable guard coupled to the tubular base and sized to cover the piercing tip of the initial access structure.

4. The dialysis access of claim 1, wherein the piercing tip is separable from the initial access structure.

5. The dialysis access of claim 1, further comprising a safety sleeve to at least partially cover the initial access structure in the withdrawn position.

6. The dialysis access of claim 5, wherein the safety sleeve disengages from the tubular base in response to withdrawal of the initial access structure.

7. The dialysis access of claim 1, wherein the seal comprises a single membrane.

8. The dialysis access of claim 1, wherein the seal comprises a plurality of membranes.

9. The dialysis access of claim 1, wherein the persistent access structure comprises one or more backeyes formed in the persistent access structure.

10. The dialysis access of claim 1, wherein the tubular base further comprises a junction portion comprising a withdrawal leg and a fluid flow leg, the withdrawal leg having a linear geometry and the fluid flow leg having a non-linear geometry.

11. A method comprising:
    inserting a dialysis access at a treatment location with an initial access structure in an extended position;
    withdrawing the initial access structure to a withdrawn position leaving a persistent access structure in place at the treatment location, the initial access structure being withdrawn from the extended position to a withdrawn position through a seal which surrounds the initial access structure in the extended position;
    capturing a piercing tip of the initial access structure at a seal of the dialysis access while withdrawing the initial access structure;
    performing a treatment; and
    removing the dialysis access from the treatment location.

12. The method of claim 11, wherein withdrawing the initial access structure to the withdrawn position comprises separating the initial access structure from the dialysis access.

13. The method of claim 11, wherein withdrawing the initial access structure to the withdrawn position comprises disengaging the initial access structure from the persistent access structure without separating the initial access structure from the dialysis access.

14. The method of claim 11, wherein withdrawing the initial access structure to the withdrawn position comprises separating a piercing tip of the initial access structure from the initial access structure and retaining the piercing tip in the dialysis access.

15. The method of claim 11, further comprising engaging the initial access structure with the seal of the dialysis access in the extended position and wherein withdrawing the initial access structure to the withdrawn position disengages the seal from the initial access structure to isolate at least a portion of the initial access structure from a fluid flow path within the dialysis access.

16. The method of claim 15, wherein the seal isolates the at least the portion of the initial access structure from the fluid path by closing an overlapping plurality of membranes.

17. The method of claim 15, wherein the seal isolates the at least the portion of the initial access structure from the fluid path by closing a flexible aperture in a membrane.

18. The method of claim 11, further comprising disengaging a removeable guard from the dialysis access to expose the initial access structure in the extended position.

19. The method of claim 11, further comprising engaging a safety sleeve to cover the initial access structure in the withdrawn position.

20. The method of claim 19, wherein the safety sleeve disengages from the dialysis access to cover the initial access structure in response to withdrawing the initial access structure from the dialysis access.

* * * * *